United States Patent [19]

Pier

[11] Patent Number: 5,284,652
[45] Date of Patent: * Feb. 8, 1994

[54] DERMATOPHYTE VACCINE

[76] Inventor: Allan C. Pier, P.O. Box 3806, Laramie, Wyo. 82071

[*] Notice: The portion of the term of this patent subsequent to Jan. 11, 2011 has been disclaimed.

[21] Appl. No.: 603,555

[22] Filed: Oct. 26, 1990

[51] Int. Cl.$^5$ .......................... A61K 39/00; C12N 1/14
[52] U.S. Cl. .................................. 424/88; 424/93 Q; 435/171; 435/242; 435/254.1; 435/911
[58] Field of Search ............... 424/88, 93 Q; 435/242, 435/254.1, 911

[56] References Cited

U.S. PATENT DOCUMENTS 4,229,434 10/1980 Sarkisov et al. ...................... 424/88

OTHER PUBLICATIONS

Propst et al, *Infection and Immunity*, vol. 20, pp. 136–141, Apr. 1978.

*Primary Examiner*—Michael G. Wityshyn
*Assistant Examiner*—Abdel A. Mohamed
*Attorney, Agent, or Firm*—Rothgerber, Appel, Powers & Johnson

[57] ABSTRACT

A vaccine for the prophylaxis of dermatophyte infection in animals, such as horses and guinea pigs, comprising a suspension of two strains of killed *T. equinum* in an effective amount combined with an adjuvant. The vaccine of the invention contains advantages over prior art dermatophyte vaccines in that it reduces the risk of infection in inoculated animals and persons utilizing the vaccine and provides cross-immunity to dermatophytes other than *T. equinum*.

6 Claims, No Drawings

DERMATOPHYTE VACCINE

BACKGROUND OF THE INVENTION

The present invention relates to the vaccination of horses and other animals against contagious infections caused by *Trichophyton equinum* (i.e., *T. equinum*) and other dermatophytes. A novel vaccine has been prepared comprising a suspension of mycelial elements and spores of the "killed" dermatophyte *T. equinum* along with an adjuvant material (i.e., immunologic stimulator) that enhances the vaccine's effectiveness. The vaccine is effective in prophylaxis of *T. equinum* infections in horses and other animals and provides cross-immunity to successful attack from other dermatophytes (e.g., *Microsporum canis*).

1. Field of the Invention

Dermatophytoses are contagious, infectious diseases of man and other mammals caused by a group of keratinophilic, parasitic fungi known as "dermatophytes." Although they are not debilitating or fatal, dermatophytoses are among the most prevalent of human and animal infectious diseases. Millions of adults and children in the United States suffer from one or more types of dermatophyte infection. The dermatophytes that characteristically infect animals (i.e., zoophilic dermatophytes) are highly contagious; they persist in the environment as infectious spores for years, and they often transfer from infected animals to their human attendants as zoonotic infections. As a result they constitute a substantial public health hazard.

Dermatophyte infections can affect various keratinized tissues, such as, the hair and stratum corneum of the skin causing areas of hair loss, scaliness and cutaneous inflammation. The most frequent dermatophyte infection in animals is called "ringworm" (i.e., infections of the skin or hair); the most frequent dermatophyte infection in man is "athlete's foot" (i.e., infections of that appendage). These diseases are a consequence of the host animal's reaction to the dermatophyte as well as the invasion of the animal's tissues by the fungus. Although the disease can generally be treated, treatment may take weeks or months to completely resolve the condition. Ringworm is unsightly, at best, and in severe cases can result in the generation of disfiguring scar tissue. It has been estimated in recent years that approximately $150,000,000 is spent annually in the United States on the treatment of ringworm.

Ringworm infections in humans and animals can be caused by a number of dermatophytes that reside on various animals, such as horses, cattle, pigs, dogs and cats. Hair and other skin fragments or debris infected with dermatophytes are lost by infected animals and contaminate the premises where these animals are maintained. Contamination may last for as much as four years. People, such as handlers, who come in contact with the animals or the premises can become carriers for the fungus to other animals or humans. Because ringworm is a world-wide problem and is transmitted between animals and man, the World Health Organization has attempted to diminish the contacting of viable dermatophytes by persons handling animals through reduction of the incidence of infection in animal populations.

In addition to the health consequences to man, the incidence of dermatophyte infections in animals can cause serious consequences for animal owners. Animals infected with dermatophytes are excluded from the sale or show ring and from competitive events, such as, horse races. Because dermatophyte infections spread rapidly among animals, entire herds, kennels or stables full of animals may become involved when infection in one or more animals is observed. In animals bred for their meat, infection with dermatophytes may result in a diminished rate of weight gain. Although griseofulvin administered orally or as a feed additive may be used to treat certain types of infected animals, it takes long periods of treatment (e.g., one to two months) to be effective, it can be prohibitively expensive where an entire herd is involved and it may also raise concerns if the animals are used to supply meat or dairy products for human consumption.

In particular, equine ringworm, caused by *T. equinum* is a highly contagious infection among horses and is transmissible also to human handlers. It transmits readily to susceptible horses by contact, brushes, blankets and other tack, wooden posts and fixtures and other items containing infectious hair or scales. Transmission is especially accelerated among horses held in close proximity to one another (i.e., in stables, corrals, etc.). Infected horses are banned from race tracks and show arenas and may be barred from crossing state or international boundaries. Infection has been a particular problem among wild horses gathered under the Bureau of Land Management wild horse program.

2. Description of the Prior Art

Because dermatophytes are wide spread parasitic agents and because infection eventually engenders acquired immunity in affected individuals, prophylactic use of immunizing agents is indicated to reduce the susceptibility of animal (or human) populations to these infections. It is recognized, however, that:

[n]o subject in the field of medical mycology has evoked more controversy than "immunity and resistance" in dermatophyte infections. The voluminous literature begins in the early nineteen hundreds and continues to accumulate unabated to the present day ... There is no single, clear-cut mechanism that will explain all aspects of susceptibility and immunity to dermatophyte infection. (Rippon, "Medical Mycology: the Pathogenic Fungi and the Pathogenic Actinomycetes," W. B. Saunders Company (3rd Ed. 1988), p. 231.)

As reported in Rippon, immunization by injection of live or killed fungi, their extracts, or their metabolic products has been attempted many times in animals. However, the author notes that the challenge with a homologous organism results only in attenuation of the disease. Resistance is transitory, and complete susceptibility returns after a few months. Rippon's conclusions appear to be based in whole or in part on A. W. Lepper, "Immunological Aspects of Dermatomycoses in Animals and Man," *Rev. Med. Vet. Mycol.*, 6:432–42 (1969), which itself is a review of the literature on dermatophyte immunity. See also, S. F. Grappel, "Immunology of Dermatophytes and Dermatophytosis," *Bacteriological Reviews*, 38: 222–50 (1974).

Prior to the present invention there has been no commercially practicable vaccine for the prevention of ringworm in horses. Prophylaxis (i.e., reduced incidence and severity) of *T. equinum* infection in horses using a vaccine comprising a suspension of viable *T. equinum* material is disclosed in U.S. Pat. No. 4,229,434 to Sarkisov et al. However, there are several defects with that vaccine. First, because it is viable it may cause localized infection at the injection site. Second, because the vaccine is live, it cannot be incorporated with other adjuvant materials frequently utilized to enhance immunologic response. Finally and of most significance, there are serious concerns about the infection of handlers and other animals contacted externally with the vaccine, since the vaccine contains "live," i.e., active, *T. equinum*. For these reasons the vaccine has not been accepted for use in certain European countries or in the United States.

At the present time, there is no known vaccine for prophylaxis of *T. equinum* in horses or other animals which is effective and does not pose a risk of infection to handlers and animals contacted externally with the vaccine.

SUMMARY OF THE INVENTION

An object of the present invention is to provide a vaccine for the prophylaxis of *T. equinum* and other dermatophyte infection in horses and other animals which is safe and is inexpensive to produce.

It is a further object of this invention to provide an improved method for vaccinating horses and other animals in the prophylaxis of *T. equinum* which method is safe to human handlers.

A further object of the present invention is to provide an improved method of producing a vaccine for prophylaxis of *T. equinum* and other dermatophyte infection in horses and other animals which is economical.

With these and other objects in mind, I have now discovered that a vaccine according to the present invention can be prepared comprising a suspension of mycelial elements and spores of one or more killed strains of *T. equinum* in an effective amount along with an adjuvant material (i.e., immunologic stimulator) that enhances the vaccine's effectiveness.

The invention also comprises an improved vaccination method provided by inoculating the horse or other animal with the vaccine of this invention on two occasions separated by approximately 10 days to three weeks. Additional benefits can be obtained by a further inoculation with the vaccine of this invention approximately four to six months after the second injection.

Finally, the objects of the present invention may be achieved by preparing a vaccine by isolating one or more strains of *T. equinum*, killing the dermatophyte strains and combining the mycelial elements and spores of the killed strains in a suspension with an adjuvant material.

Further objects and features of the present invention may be apparent from the disclosure of this specification as set forth herein.

DETAILED DESCRIPTION AND PREFERRED EMBODIMENT

1. The Vaccine

A vaccine for prophylaxis of *T. equinum* infection in horses is prepared as a suspension comprising conidia (i.e., spores) and other mycelial elements of killed *T. equinum* in an effective amount along with an adjuvant material.

One or more strains of *T. equinum* can be utilized in the vaccine. In the preferred embodiment of this invention described below, two strains of *T. equinum* are utilized. It is anticipated that the use of multiple strains may provide further immunity or resistance to challenge from active *T. equinum*. The use of two or more strains helps to ensure the requisite immunity and resistance.

The vaccine strains of the present invention were isolated from clinical cases of equine ringworm. This was accomplished by plucking scales and hairs from typical lesions and inoculating them on to "C & C" medium (i.e., "Soytone" manufactured by Difco) dextrose agar containing cyclohexamide and chloramphenicol; 0.5 g. and 0.05 g. per liter respectively). The cultures were incubated (at room temperature) until colonies of *T. equinum* appeared 7 to 10 days later. Single colonies were picked and transferred to new medium and grown to assure purity of the isolate. The isolate identity was assured by microscopic examination for typical morphology and by nutritional tests showing a requirement for nicotinic acid.

In the preferred embodiment the vaccine of this invention is prepared using conidia and mycelial elements of two strains of *T. equinum*, both of which were clinical isolates from infected horses that showed areas of hair loss, scaly dermatitis and ectothrix formation. The two vaccine producing strains had different physical appearances on culture media.

*T. equinum* strain R.S. was obtained from an epidemic of dermatophyte infection on horses in Rock Springs, Wyo. This strain grows as a flat, white, cottony colony with a reddish-brown reverse pigmentation. Microconidia are abundantly produced, but macroconidia are rare. Inoculum materials corresponding to the 5th to 6th passage on laboratory medium are preserved in refrigerated suspensions and in lyophilized stock cultures.

*T. equinum* strain B.F. was obtained from an epidemic of dermatophyte infection on horses in Bloomfield, Neb. This strain grows as a flat buff to brown, granular colony with a reddish-brown reverse pigmentation. Microconidia are produced in great abundance, but macroconidia are rare. Inoculum materials corresponding to the 4th to 5th passage on laboratory medium are preserved in refrigerated suspensions and in lyophilized stock cultures.

Both strains of *T. equinum* cause dermatophytosis when experimentally inoculated on to clipped areas of guinea pigs and rubbed into the inoculation site. Both strains of *T. equinum* grow on casein basal medium supplemented with nicotinic acid, but neither grows on vitamin free casein basal medium (i.e., a standard nutritional test for *T. equinum* identification). Antigenic differences have not been observed between the two strains in gel diffusion precipitin tests or in delayed cutaneous hypersensitivity tests using culture filtrate antigens prepared from the separate strains.

The *T. equinum* strain or strains used in the vaccine are killed. The suspension is standardized optically (i.e., by light transmittance) to assure reproducibility of concentration. Before inactivation, the vaccine typically contains approximately $1 \times 10^7$ colony forming units/ml. of one or more strains of *T. equinum*. This approximates 4 mg. of *T. equinum*/ml. Either before or after inactivation, the suspension can be optically standardized to approximately 2.5 to 5.0% T. at 540 mµ to ensure the concentration. It is anticipated that the concentration of *T. equinum* in the suspension and in final vaccine can be varied provided that an effective amount of killed dermatophyte is delivered by vaccination.

Because the dermatophyte component of the vaccine has been killed, it is possible to combine it with a commercial adjuvant. A commercial adjuvant cannot be utilized with live vaccines, such as that disclosed in the patent of Sarkisov et al., because the live dermatophyte component cannot be lyophilized with the adjuvant, and the adjuvant would interfere with the viability and stability of the dermatophyte.

It appears that most commercial adjuvants may be used as a vehicle to suspend the "killed" components of *T. equinum* in the present invention. These adjuvants include a number of commercially available materials that are useful in suspending the dermatophyte component and stimulating the vaccinated animal's immune system response. Examples of acceptable adjuvants include:

(a) "Quil A" is a commercially available adjuvant manufactured by Sargent Chemical Co., Clifton, N.J. Quil A is a purified saponin extract from the bark of the Quillaja Saponaria Molina tree. It is currently used as a suspension medium in a number of animal vaccines throughout the world, such as, utilized in the prevention of foot and mouth Quil A is the preferred material for use in because it is widely used, readily available not very expensive. It also creates very stable mixture do not separate.

(b) "Freund's Incomplete is manufactured by many biologics producers (e.g., Chemical Co., St. Louis, Mo.). It is comprised primarily of light mineral oil.

(c) A number of anhydrous based materials, such as "Lipovant" (sold by Accurate C and Scientific Co., Westbury, N.Y.) which consists of oil and lecithin mixture which emulsifies quite well.

(d) Aluminum hydroxide by a number of companies including Accurate Chemical and Scientific Co.

Quil A is a water soluble that mixed readily with the vaccine in an amount of 150 mg./1. of killed *T. equinum* suspensions. Freund's incomplete adjuvant and aluminum hydroxide gel are approximately 1:1 on a volume basis with the *T. equinum* and Lipovant is used 1 ml. to 8 ml. of the suspension In the preferred embodiment of the invention, Quil A is used as the adjuvant. The resulting vaccine comprising billed *T. equinum* and Quil A with *T. equinum* being present in an amount of approximately 4 mg./ml. This vaccine has proven to be effective in dosages of approximately 5.0 ml. for horses and 0.5 ml. for guinea pigs.

2. Methods of Producing the Vaccine

In general the vaccine is prepared by preparing an appropriate suspension of the strain or strains of *T. equinum* to be utilized, killing the dermatophyte material and adding an adjuvant to the suspension of killed dermatophyte material. The basic steps are described in more detail, as follows:

(a) Culture media, culture and harvest. One or more strains of *T. equinum* are on solid medium ($M_4OY$) containing cyclohexamide, chloramphenicol and nicotinic acid (0.5g., 0.05g. and 0.4 mg per liter, respectively). The medium is dispensed into cotton stoppered flasks (250 ml. per 2-liter flasks), allowed to at room temp (25° to 27° C.) for 1 week and then inoculated with a 3 ml. suspension (10% T) of the desired vaccine strain(s). If more than one strain of *T. equinum* is utilized, a separate flask is used for each strain. 3 to 6 weeks' growth (25° to 27° C.), 100 ml. sterile buffered saline (PBS pH 7.4) is added to the flask and the surface growth (conidia and mycelium) is washed using a sterile brush. The suspension is filtered through gauze to remove large particles. A portion of the suspension is cultured on Sabouraud's dextrose agar, on BHI agar, vitamin free casein basal agar ("CBA") and on plus nicotinic acid to check the purity of the harvested growth (b) Inactivation: The suspension is then inactivated by adding thimerosal (1:10,000). After standing 24 to 48 hours, the suspension is by centrifugation, the supernatant fluids discarded and the sedimented mycelial elements are (PBS plus thimerosal 1:10,000) and optically (2.5 to 5% T at 540 mμ). The standardized suspensions are sterility checked by subculture on Sabouraud's dextrose agar and BH1 blood agar.

(c) Adjuvant addition: Following satisfactory results on purity check cultures on sterility check cultures (after inactivation), the standardized suspension is combined with an adjuvant (i.e Quil A 150 mg./1.), bottled in sterile vaccine vials appropriately labeled.

3. Application of the Vaccine/Testing

In general, the vaccine be administered to horses in two injections (5 ml. each) given intramuscularly at 10-day to 3-week intervals. A dose is recommended after approximately 4 6 months. These dosages are based on a killed *T. equinum* concentration of 5% T. (c. 4 mg./ml.). Use of a more concentrated vaccine would permit reduction of the dose that an equivalent amount of killed de material is introduced in each injection.

Two methods have been employed for testing the potency of the vaccine: experimental challenge and delayed cutaneous hypersensitivity.

Experimental challenge: As example of this method, two weeks after the second vaccine, a group (10 or more) of vaccinated guinea pigs a similar group of unvaccinated guinea pigs are challenged by a virulent suspension of *T. equinum* or *M. canis* (or other dermatophyte depending on the test required is plucked from an area approximately 1 $cm^2$. on the animal's back, then an area approximately 4 $cm^2$. centering plucked area is clipped. Inoculum (0.1 ml. of 10 suspension approximating $5\times10^6$ cfu./ml.) is into the clipped and plucked areas (6 to 12 a sterile rubber bulb). The animals are observed over a 3 to 4 week post-inoculation period for development. Hairs plucked from lesion are examined microscopically for invasion of the hairshaft and/or scales by dermatophytic mycelia and for the development of ectothrix. The microscopic appearance is graded 3+ depending on: 0 = no detectable hair or scale ; 1 = minimal mycelial invasion of hair or 2 = mycelial invasion plus occasional ectothrix; 3 = f ectothrix. The skin of the inoculated area of each is brushed with a sterile, natural fiber brush which is then used to inoculate C & C agar medium for fungal identification. The results of vaccinated animals are to those from non-vaccinated, challenged control animals. The total test takes approximately 2 months from injection and entails use of infectious material and subjective results.

Delayed cutaneous hypersensitivity ("DCH") skin test. This test is more rapid, does not use of infectious materials (i.e., contagious to handlers) and provides an objective measurement of vaccine potency. Two weeks after the second vaccination, pigs (vaccinated and control groups) are skin tested 0.1 ml. intradermal injections of skin test antigens skin test antigen used is grown on neopeptone dialysate inoculated with the specific dermatophyte strain and on a rotary shaker at 37° C. for 3 weeks. The filtrate is preserved [thimerosal 1:10,000]used as the skin test sensitin. These sensitins can be by dilution or concentration for a desired in sensitized animals.) Twenty-four hours after intrade injection, the induration at the injection site measured (calibrated calipers) and compared to the normal skin thickness. The resulting difference (induration minus normal skin thickness) constitutes the hypersensitivity ("DCH") response engendered by The test is significant because cell mediated response is considered the main basis of immunity. This test takes approximately one month conduct after the initial inoculation.

A number of significant bene have been observed from the use of the vaccine of the present invention.

First, the vaccine of the invention is safer to use than viable vaccines for several reasons. One of these is that the vaccine does not permit local infection to occur at vaccination sites in immunized or on the skin or hands of vaccinators. The use of vaccine renders such infections virtually and none have been reported to date in the use and of the vaccine. In addition, the vaccine does not survival and transmission of other infectious that might gain access to the preparation (e.g., or viral agents) or permit reversion to virulence "viable, non-virulent" fungal immunogens.

Second, controlled studies laboratory animals and horses have demonstrated that the vaccine dramatically increases the resistance to both infection and contact exposure infection. In that did become infected, the disease was substantially reduced in severity. Tests performed to date that the vaccine is at least as, if not effective than the use of a live, i.e., active, vaccine also disclose that the vaccine may be effective for as one year. Sufficient information is not at this time to determine whether the protection for a longer duration without an additional booster.

Finally, and unexpectedly, significant cross immunity for other dermatophytes (e.g., *Trichophyton mentogrophytes*, *Microsporum canis* and *Microsporum equinum*) has been demonstrated in laboratory immunized with this vaccine through development of cross reacting antibodies and cross reactions in delayed cutaneous hypersensitivity (DCH) skin tests. Further, cross to experimental challenge infection by *M. canis* was developed in guinea pigs vaccinated with the killed *T. equinum* vaccine of this invention..

4. Specific Examples

Example 1 —Immunity in Horses

Immunity in horses engendered by the *T. equinum* vaccine was tested by vaccinating 20 hors (colts 1 year old or less) two times (5 ml. each) with to 14 days between the initial and final injections. Th comprised a killed suspension of *T. equinum* R.S. and B.F. (5% T.) and Quil A as an adjuvant as described previously. Following the final the horses were included with 10 comparable horse as non-vaccinated controls. Fourteen donor (i.e., infected) horses were included to provide a source of infection. The horses were managed to maximize exposure infection (i.e., passed daily through a chute containing to transfer infected hairs and scales from to non-infected animals.) The horses were monthly for 3 months for development of lesions and score . lesion frequency (i.e., 0 =no lesions; 1 =a single lesion; 2=2-3 typical lesions; 3 =multiple typical over body.) Lesions were examined culturally by the lesion with a sterile brush which was then us inoculate culture medium. Microscopic examination conducted on hairs plucked from lesions. The vaccine 90 percent of the vaccinated horses from lesion development. Sixty percent of the non-vaccinated developed lesions. Vaccinated horses that developed had an average score of 1, while non-vaccinated had an average score of 2. A significant level was conferred by the vaccine.

Example 2 —Live v. Killed Vaccine

Two different samples of vaccine were prepared utilizing *T. equinum* strain R.S. at 5% T. A suspension of this material was prepared in PBS. As to one portion of the suspension, the *T. equinum* was killed and combined with Quil A as an adjuvant, as described above. In the other portion, the *T. equinum* was not killed and no adjuvant was added.

The vaccines were compared Groups of 8 to 10 guinea pigs were given one (1×) or 2 (2×) doses of the live or killed preparations by int injection (0.5 ml. vaccine per dose). Two between the injections in the 2× groups. All pigs were challenged by inoculation with homologous strain of *T. equinum* applied to a skin site previously prepared by plucking and clipping. The presence of infection was periodically determined as described above.

The results are shown in the following table.

TABLE I

| GROUP | NO. | CULTURE POSITIVE TOTAL OBSERVATIONS. | MEAN COLONIES OBSERVATION |
|---|---|---|---|
| Control | 9 | 6/54 | 3.8 |
| Vacc (Live 1X) | 10 | 11/60 | 4.7 |
| Vacc (Kill 1X) | 10 | 6/60 | 2.1 |
| Vacc (Live 2X) | 10 | 2/60 | 2.0 |
| Vacc (Kill 2X) | 8 | 3/48 | 1.6 |

The test demonstrated that the killed vaccine of this invention provided protection at least as good as a vaccine based on live *T. equinum.*

Example 3 —Delayed Challenge

A group of 11 horses were vaccinated with *T. equinum* vaccine as described in Example 1. Challenge occurred approximately six months after the initial dose of vaccine by pen contact with 17 unvaccinated and infected pen mates. After approximately 2 months of direct contact, the horses were examined closely for dermatophyte lesions and graded: 0 =no lesions; 1 =single typical lesion; 2=2 to 3 typical lesions; 3 =numerous typical lesions scattered over body.

The results are shown in Table II.

TABLE II

| TREATMENT | NO. | CULTURE POSITIVE | CLINICAL CLASS |
|---|---|---|---|
| Non Vaccinated | 17 | 12 | 2.5 |
| Vaccinated | 11 | 1 | 1 |

Example 4 —Long Term Herd Test

A test was performed to determine the ability of the vaccine to control ringworm infection in a herd of horses to which animals were constantly being added or withdrawn. The horses involved were wild range horses collected by the Bureau of Land Management and placed into holding pens from which horses were removed as they were sold or otherwise disposed of. At the inception of the vaccination program, ringworm infected approximately sixty percent of the horses which were put into holding pens. A practice was established of vaccinating each of the new horses added to the holding pens as described in Example 1. Over a period of approximately two years, more than two thousand new horses were vaccinated as they passed through the facility. Vaccine based on *T. equinum* strain R.S. was used for the first year (approximately one-third of the horses). Vaccine based on *T. equinum* strains R.S. and B.F. was used for the remainder of the vaccination program. Ringworm infection of the herd became virtually non-existent. Although steps were also instituted in that time period to "clean up" the surroundings, that action alone would not have been sufficient to achieve the results produced from the vaccine because of the prolonged viability of the infection in the environment. This test illustrates the long term effect of the vaccination procedure.

Example 5 —Immunity in Guinea Pigs

Guinea pigs of approximately 400 gms. in body weight were inoculated intramuscularly twice with 14 days between injections each of which contained 0.5 ml. of vaccine as described in Example 1. Two weeks after the second injection their immunity was assessed by determination of (1) development of delayed cutaneous hypersensitivity (DCH), a measure of cell-mediated immune response, (determined by injection of neopeptone dialysate culture filtrate antigen of *T. equinum* and measuring induration of the skin site with calipers; and (2) protection from challenge with virulent *T. equinum* culture and assessment of the presence or absence of resulting dermatophytosis in vaccinated vs. non-vaccinated animals. (The degree of microscopically detectable infection was graded: 0 =non detected; 1 =occasional scale and hair invasion, no ectothrix; 2 =scale invasion plus occasional ectothrix (1 or 2 hairs); 3 =frequent extensive ectothrix.)

Typically 10 guinea pigs were vaccinated as described above. These guinea pigs and 10 non-vaccinated control guinea pigs were skin tested for DCH prior to challenge inoculation. Skin test responses of vaccinates averaged 4.2 mm. compared with 0.1 mm. of controls demonstrating a strong cell-mediated immune response to *T. equinum*.

The immunity was challenged by plucking hair from 2 cm. square area and clipping the surrounding area. Challenge inoculum of *T. equinum* (0.1 ml., 5% T.; $1.4\times10^7$ C.F.U./ml.) was applied to the prepared skin area and rubbed in with 6 strokes of a rubber bulb. Infection was assessed by examination of the challenge site 10 to 14 days later for scaliness, erythema and exudative crusts. Hairs and scales were plucked from the site and examined microscopically and culturally for infection. Two of ten vaccinates and seven of ten controls showed clinical evidence of infection. The mean score of microscopic examination (as delineated above) was 0.8 for vaccinates and 2.1 for controls showing a substantial protection from expanding infection.

The skin test (DCH) is preferred as a measure of vaccine efficacy and potency since it provides a more objective, quantitative measurement, substantially shortens the time of the test and avoids infectious hazard to laboratory personnel.

Example 6 —Cross Immunity in Laboratory Animals

Cross immunity in laboratory animals (guinea pigs) vaccinated with *T. equinum* was determined by testing serums for cross reacting antibodies (gel diffusion precipitin test) and for DCH. Substantial cross humoral and cell-mediated immunity was established in guinea pigs vaccinated with killed *T. equinum* vaccine (5% T.) and Quil A to antigens of *T. mentagrophytes, T. verrucosum, Microsporum canis, M. equinum* and *M. gypseum*. A reduced susceptibility to infection was observed in guinea pigs vaccinated with *T. equinum* vaccine and challenged with virulent cultures of *M. canis*.

Serums of guinea pigs immunized 2 to 3 times with the *T. equinum* vaccine (as described in Example 1) regularly produced 1 to 2 precipitin lines when tested with concentrated (10×) neopetone dialysate culture filtrate antigens of *T. equinum, T. verruscosum. T. mentagrophytes, M. canis, M. equinum* and *M. gypseum* in a standard gel diffusion precipitin test. Skin tests for DCH conducted in guinea pigs after 2 vaccinations showed increments of induration (in mm.) over normal skin of 1.5, 0.5, 0.7, 0.4 and 0.2 for the respective antigens of *T. equinum, T. verruscosum, T. mentagrophytes. M. canis, M. equinum*.

The results of protection of animals vaccinated with *T. equinum* vaccine and challenged with a virulent culture of *M. canis* are showed in Table III.

TABLE III

Virulent *M. canis* Challenge Results

| Treatment | Infected | Infection Score | Average Number of Colonies |
|---|---|---|---|
| *T. equinum* vaccine | 7/10 | 1.45 | 55 |
| Non-vaccinated | 10/10 | 2.85 | 75 |

Thus, the *T. equinum* vaccine imparted substantial cross-immunity to *M. canis* as seen by serologic cross-reaction to precipitin tests, DCH skin test sensitivity and reduced invasiveness of infection (i.e., reduced infection score).

I claim:

1. A vaccine for the prophylaxis of *T. equinum* in horses which provides detectable cross-immunity to other equine dermatophyte pathogens and which poses minimum risk of infection to man and other animals exposed to the vaccine comprising a suspension of two strains of killed dermatophytes of *T. equinum* in an effective amount combined with an adjuvant.

2. The vaccine according to claim 1 in which the *T. equinum* is present in an amount of 2.5 to 5% light transmittance at 540 mμ.

3. The vaccine according to claim 1 in which the adjuvant is selected from the group consisting of Quil A, anhydrous lipids, Freund's incomplete adjuvant and aluminum hydroxide.

4. The vaccine according to claim 3 in which the adjuvant is Quil A.

5. A process for the prophylaxis of *T. equinum* in horses which provides detectable cross-immunity to other equine dermatophyte pathogens and which poses minimum risk of infection to man and other animals exposed to the vaccine comprising inoculating the horse intramuscularly with a first inoculation of 5 ml. of a vaccine as claimed in claims 1, 3 or 8, and 10 days to three weeks after the first inoculation, inoculating the horse with a second inoculation of 5 ml. of said vaccine.

6. The process according to claim 5 including inoculating the horse with a third intramuscular inoculation of the same amount of said vaccine administered four to six months after the first and second inoculations.

* * * * *